(12) United States Patent
Fujimori et al.

(10) Patent No.: US 9,155,309 B2
(45) Date of Patent: *Oct. 13, 2015

(54) VIRUS INACTIVATING SHEET

(75) Inventors: Yoshie Fujimori, Tokyo (JP); Youhei Jikihara, Tokyo (JP); Tetsuya Sato, Tokyo (JP); Yoko Fukui, Tokyo (JP); Tsuruo Nakayama, Tokyo (JP)

(73) Assignee: NBC MESHTEC, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/395,691

(22) PCT Filed: Oct. 4, 2010

(86) PCT No.: PCT/JP2010/005931
§ 371 (c)(1),
(2), (4) Date: Mar. 23, 2012

(87) PCT Pub. No.: WO2011/040048
PCT Pub. Date: Apr. 7, 2011

(65) Prior Publication Data
US 2012/0171276 A1 Jul. 5, 2012

(30) Foreign Application Priority Data
Oct. 2, 2009 (JP) ................................. 2009-230946

(51) Int. Cl.
*A01N 59/20* (2006.01)
*A01N 25/34* (2006.01)
*A01N 59/16* (2006.01)
*A01N 59/18* (2006.01)
*A41D 19/015* (2006.01)
*A42C 5/00* (2006.01)
*A43B 23/00* (2006.01)
*A01N 59/12* (2006.01)
*A61K 33/18* (2006.01)
*A61K 33/34* (2006.01)
*A61L 31/16* (2006.01)
*A61L 15/44* (2006.01)
*B32B 5/16* (2006.01)
*D06M 11/00* (2006.01)
*D01F 1/10* (2006.01)
*D21H 21/36* (2006.01)
*D21H 27/20* (2006.01)
*D06M 11/11* (2006.01)
*D06M 16/00* (2006.01)
*D06M 23/08* (2006.01)
*D06N 7/00* (2006.01)
*D06M 101/06* (2006.01)

(52) U.S. Cl.
CPC ................ *A01N 59/12* (2013.01); *A01N 25/34* (2013.01); *A01N 59/20* (2013.01); *A61K 33/18* (2013.01); *A61K 33/34* (2013.01); *A61L 15/44* (2013.01); *A61L 31/16* (2013.01); *B32B 5/16* (2013.01); *D01F 1/103* (2013.01); *D06M 11/00* (2013.01); *D06M 11/11* (2013.01); *D06M 16/00* (2013.01); *D06M 23/08* (2013.01); *D06N 7/0039* (2013.01); *D21H 21/36* (2013.01); *D21H 27/20* (2013.01); *A61L 2300/102* (2013.01); *A61L 2300/408* (2013.01); *D06M 2101/06* (2013.01); *D06M 2400/01* (2013.01)

(58) Field of Classification Search
CPC combination set(s) only.
See application file for complete search history.

(56) References Cited

U.S. PATENT DOCUMENTS

| | | | |
|---|---|---|---|
| 6,451,333 | B1 | 9/2002 | Beerse et al. |
| 2004/0091550 | A1 | 5/2004 | Tomasgaard et al. |
| 2006/0127457 | A1* | 6/2006 | Buchalter ............... 424/443 |
| 2008/0311165 | A1 | 12/2008 | Gabbay |
| 2009/0094954 | A1 | 4/2009 | Nakayama et al. |
| 2010/0003528 | A1* | 1/2010 | Rozhin et al. ........... 428/429 |
| 2010/0040655 | A1 | 2/2010 | Ren et al. |
| 2011/0262513 | A1* | 10/2011 | Fujimori et al. .......... 424/411 |
| 2012/0192876 | A1 | 8/2012 | Fujimori et al. |

FOREIGN PATENT DOCUMENTS

| | | |
|---|---|---|
| DE | 10 2007 003 662 | 7/2008 |
| EP | 362448 A1 * | 4/1990 |
| JP | 2005-082902 | 3/2005 |
| JP | 2005-264347 | 9/2005 |
| JP | 2006-61320 | 3/2006 |
| JP | 2006-63160 | 3/2006 |
| JP | 2006-291031 | 10/2006 |
| JP | 2006-328039 | 12/2006 |
| JP | 2007-039395 | 2/2007 |
| JP | 2007-039396 | 2/2007 |
| JP | 2009-018503 | 1/2009 |
| WO | 01/28337 | 4/2001 |

(Continued)

OTHER PUBLICATIONS

International Search Report issued Dec. 21, 2010 in International (PCT) Application No. PCT/JP2010/005931.
International Preliminary Report on Patentability issued May 8, 2012 in International Application No. PCT/JP2010/005931, of which the present application is the national stage.
Extended European Search Report issued Nov. 5, 2013 in corresponding European Application No. 10820169.0.

(Continued)

*Primary Examiner* — Kyle Purdy
(74) *Attorney, Agent, or Firm* — Wenderoth, Lind & Ponack, L.L.P.

(57) ABSTRACT

A virus inactivating sheet is provided that can inactivate viruses adhering thereto even in the presence of lipids and proteins regardless of whether or not the viruses have an envelope. The virus inactivating sheet can inactivate viruses adhering thereto and includes a sheet body, and monovalent copper compound fine particles and/or iodide fine particles that are held by the sheet body. The virus inactivating sheet can inactivate various viruses. These viruses can be inactivated even in the presence of lipids and proteins.

12 Claims, 3 Drawing Sheets

(56) References Cited

FOREIGN PATENT DOCUMENTS

| WO | 2007/080804 | 7/2007 |
| WO | 2007/093808 | 8/2007 |
| WO | WO 2007102334 A1 * | 9/2007 |
| WO | 2008/029387 | 3/2008 |
| WO | 2010/026730 | 3/2010 |
| WO | WO 2010073738 A1 * | 7/2010 |

OTHER PUBLICATIONS

Borkow et al., "Putting Copper Into Action: Copper-Impregnated Products with Potent Biocidal Activities," The FASEB Journal, 2004, pp. 1-19.

* cited by examiner

VIRUS INACTIVATING SHEET

This application is a U.S. national stage of International Application No. PCT/JP2010/005931 filed Oct. 4, 2010.

TECHNICAL FIELD

The present invention relates to a virus inactivating sheet. In particular, the invention relates to a virus inactivating sheet that can inactivate various viruses adhering thereto even in the presence of lipids and proteins regardless of whether or not the viruses have an envelope.

BACKGROUND ART

In recent years, deaths have been reported that are caused by viral infections such as SARS (severe acute respiratory syndrome), noroviruses, and avian influenza. At present, because of developments in transportation and mutation of viruses, the world faces the risk of a "pandemic" that is an epidemic of viral infection throughout the world, and there is an urgent need for countermeasures. To deal with such a situation, the development of vaccine-based antiviral drugs is hastened. However, since vaccines have their own specificity, they can only prevent infection with specific viruses. At hospitals and clinics, nosocomial infection is a serious problem, and this is also being recognized as a social problem. The nosocomial infection is contagious infection with MRSA (methicillin-resistant *Staphylococcus aureus*) brought into a hospital by a carrier or an infected person or with MRSA strains of *Staphylococcus aureus* that are caused by antibiotic administration. Such contagious infection occurs from a patient directly to other patients and health professionals or through the health professionals, used articles such as white coats, pajamas, and bed sheets, or an environment including walls and facilities such as air conditioners. Therefore, there is a strong demand for the development of an antiviral member capable of exhibiting bactericidal and antiviral effects effective for various viruses and bacteria.

As means for solving the foregoing problems, there is a virus inactivating sheet that uses a composite body composed of a resin containing thereinside inorganic porous crystals that support antibacterial metal ions such as silver ions or copper ions (Patent Literature 1). Virus inactivating agents containing iodide-cyclodextrin clathrate compounds dissolved therein have been reported (Patent Literatures 2, 3, and 4).

CITATION LIST

Patent Literature

Patent Literature 1: Japanese Patent Application Laid-Open No. 2006-291031
Patent Literature 2: Japanese Patent Application Laid-Open No. 2006-328039
Patent Literature 3: Japanese Patent Application Laid-Open No. 2007-39395
Patent Literature 4: Japanese Patent Application Laid-Open No. 2007-39396

SUMMARY OF INVENTION

Technical Problem

The method that uses a resin containing thereinside inorganic porous crystals is applicable to fibrous fabrics. However, this method is not applicable to films and sheets that do not use fibers and to inorganic materials. The virus inactivating agent that uses iodine is water-soluble. Therefore, when a fabric or a sheet is impregnated with such a virus inactivating agent, if the fabric or sheet is moistened with water, the components thereof easily dissolve in water.

Viruses can be classified into those having no envelope such as noroviruses and those having an envelope such as influenza viruses. Even though a drug can inactivate viruses having an envelope, this drug may not be effective for viruses having no envelope. When an inactivating sheet is applied to a mask or used for, for example, a surgical protective suit or a pillow case, lipids and proteins contained in bodily fluids such as blood and saliva may adhere to the inactivating sheet because it is an article used in contact with the mouth or nose of an infected person. Therefore, it is preferable that viruses can be inactivated even in an environment in which lipids and proteins are present. However, this is not verified in the above literatures.

To solve the foregoing problems, the present invention provides a virus inactivating sheet that can inactivate viruses adhering thereto even in the presence of lipids and proteins regardless of whether or not the viruses have an envelope.

Solution to Problem

A first aspect of the invention is a virus inactivating sheet that can inactivate a virus adhering thereto, the virus inactivating sheet characterized by comprising a sheet body and monovalent copper compound fine particles and/or iodide fine particles, the monovalent copper compound fine particles and/or the iodide fine particles being held by the sheet body. In the present description, the virus inactivating sheet means a sheet having an ability to inactivate viruses (to reduce the infectivity of the viruses or to deactivate the viruses). Therefore, the concept of the virus inactivating sheet includes, in addition to the sheet body used for the purpose of inactivating viruses, wallpaper sheets used for the purpose of decoration and other purposes, and the like. In the present description, the virus inactivating ability and an antiviral ability are used in the same sense.

A second aspect of the invention is the virus inactivating sheet according to the first aspect, characterized in that the monovalent copper compound fine particles are particles of at least one selected from the group consisting of a chloride, an acetate, a sulfide, an iodide, a bromide, a peroxide, an oxide, and a thiocyanate.

A third aspect of the invention is the virus inactivating sheet according to the second aspect, characterized in that the monovalent copper compound fine particles are particles of at least one selected from the group consisting of CuCl, $CuOOCCH_3$, CuI, CuBr, $Cu_2O$, $Cu_2S$, and CuSCN.

A fourth aspect of the invention is the virus inactivating sheet according to any of the first to third aspects, characterized in that the iodide fine particles are particles of at least one selected from the group consisting of CuI, AgI, $SbI_3$, $IrI_4$, $GeI_2$, $GeI_4$, $SnI_2$, $SnI_4$, TlI, $PtI_2$, $PtI_4$, $PdI_2$, $BiI_3$, AuI, $AuI_3$, $FeI_2$, $CoI_2$, $NiI_2$, $ZnI_2$, HgI, and $InI_3$.

A fifth aspect of the invention is the virus inactivating sheet according to any of the first to fourth aspects, characterized in that the monovalent copper compound fine particles and/or the iodide fine particles are held by the sheet body through a group of other inorganic fine particles that are anchored to the sheet body through chemical bonds with a silane monomer and/or a polymerization product of the silane monomer.

A sixth aspect of the invention is a bed sheet that uses the virus inactivating sheet according to any of the first to fifth aspects.

A seventh aspect of the invention is a protective suit that uses the virus inactivating sheet according to any of the first to fifth aspects.

An eighth aspect of the invention is a glove that uses the virus inactivating sheet according to any of the first to fifth aspects.

A ninth aspect of the invention is a medical drape that uses the virus inactivating sheet according to any of the first to fifth aspects.

A tenth aspect of the invention is a cap that uses the virus inactivating sheet according to any of the first to fifth aspects.

An eleventh aspect of the invention is a shoe cover that uses a virus inactivating sheet according to any of the first to fifth aspects.

A twelfth aspect of the invention is a filter that uses a virus inactivating sheet according to any of the first to fifth aspects.

A thirteenth aspect of the invention is surgical tape that uses a virus inactivating sheet according to any of the first to fifth aspects.

A fourteenth aspect of the invention is gauze that uses a virus inactivating sheet according to any of the first to fifth aspects.

A fifteenth aspect of the invention is wallpaper that uses a virus inactivating sheet according to any of the first to fifth aspects.

Advantageous Effects of Invention

The present invention can provide a virus inactivating sheet that can inactivate viruses adhering to, for example, the surface of the sheet even in the presence of proteins such as droplets and blood.

DESCRIPTION OF EMBODIMENTS

A first embodiment will next be specifically described with reference to FIG. 1.

Figure 1:
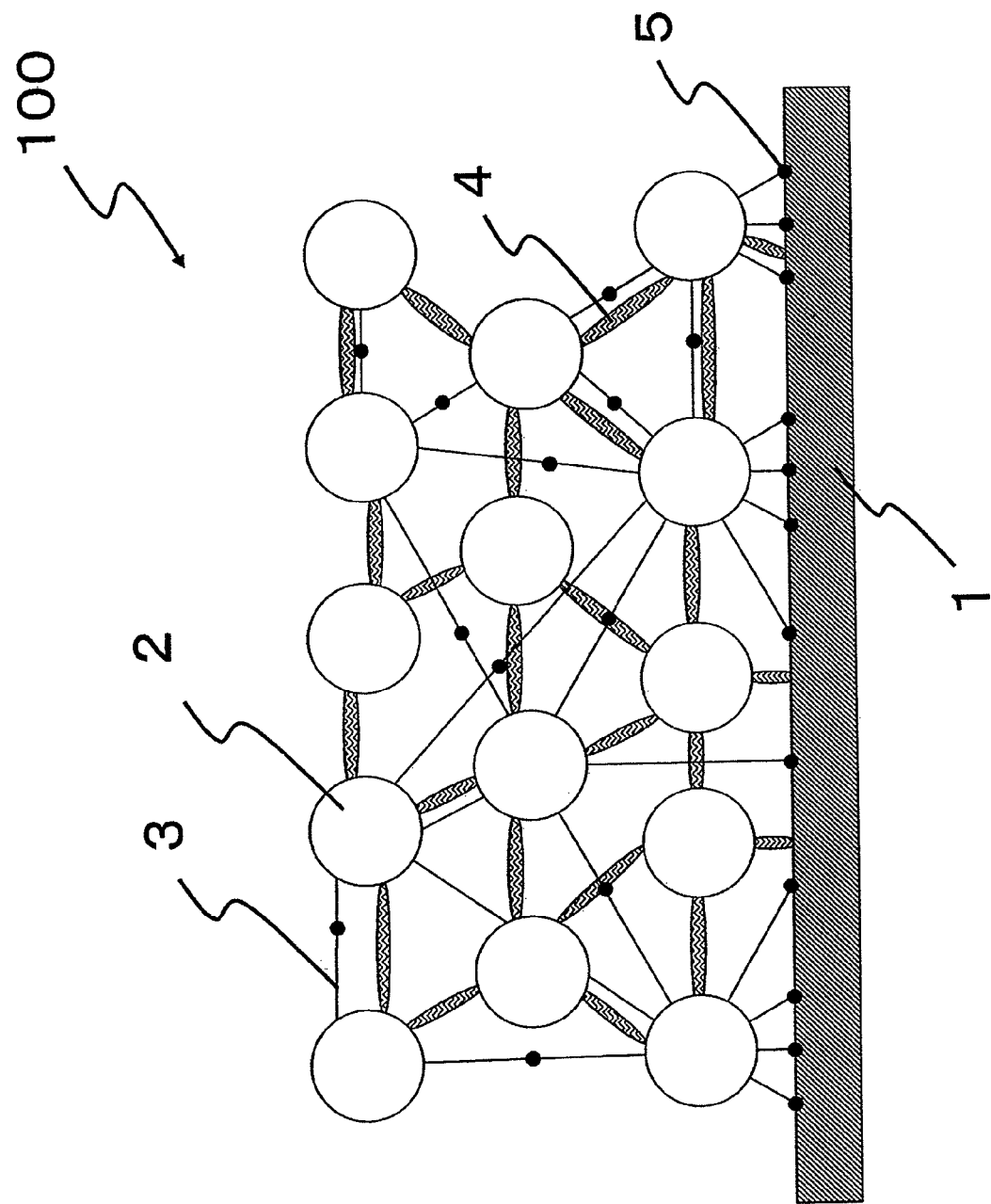
FIG. 1 is a schematic diagram of a cross-section of a virus inactivating sheet of a first embodiment.

FIG. 1 is an enlarged schematic view of apart of a cross-section of a virus inactivating sheet 100 of the first embodiment of the present invention. Inorganic fine particles 2 having a virus inactivating ability (hereinafter referred to as virus inactivating fine particles) are bound to the surface of a sheet body 1 used as a substrate through, for example, a binder. In the first embodiment of the present invention, a silane monomer or an oligomer obtained by polymerization of the silane monomer is used as the binder because of the reason described later. Therefore, in the example shown in the schematic diagram in FIG. 1, for the purpose of facilitating understanding, the virus inactivating fine particles 2 are bound to the surface of the sheet body 1 by chemical bonds 5 through a silane monomer (or a polymerized product of the silane monomer) 3. Here, a dimer is exemplified as the oligomer. In the present embodiment, a reinforcing material 4 is used to firmly anchor the virus inactivating fine particles 2 to the sheet body 1, as shown in FIG. 1. The reinforcing material 4 is added when it is necessary to firmly anchor the virus inactivating fine particles 2 to the sheet body 1 and is not necessarily added.

In the first embodiment, the virus inactivating fine particles 2 are monovalent copper compound fine particles and/or iodide fine particles and can inactivate viruses regardless of whether or not the viruses have an envelope. Therefore, the virus inactivating sheet 100 of the first embodiment can be considered to hold an antiviral agent including at least one type of inorganic fine particles selected from the group consisting of the monovalent copper compound fine particles and/or the iodide fine particles. The virus inactivating fine particles 2 of the first embodiment can inactivate viruses even in the presence of proteins and lipids.

At present, the virus inactivating mechanism of the virus inactivating fine particles 2 is not clear. The mechanism is assumed to be as follows. When the virus inactivating fine particles 2 come into contact with moisture in air or droplets, part of the virus inactivating fine particles 2 undergoes an oxidation-reduction reaction, or active species are generated. This causes some effect on the surface electric charge or DNA of the viruses adhering to the virus inactivating sheet 100 of the first embodiment, and the viruses are thereby inactivated.

No particular limitation is imposed on the size of the held virus inactivating fine particles 2, and a person skilled in the art can appropriately set the size. However, the average particle diameter is 1 nm or larger and smaller than 500 µm, preferably 1 nm or larger and smaller than 1 µm, and more preferably 1 nm or larger and smaller than 500 nm. When the average particle diameter is smaller than 1 nm, the virus inactivating fine particles 2 are physically unstable and agglutinate with each other. Therefore, it is difficult to support the particles on the sheet body 1 uniformly. When the average particle diameter is 500 µm or larger, the adhesion between the particles and the sheet body 1 is lower than that when the average particle diameter falls within the above range. In the present description, the average particle diameter is a volume average particle diameter.

No particular limitation is imposed on the type of the virus inactivating fine particles 2 serving as an active ingredient. However, the monovalent copper compound fine particles are preferably the particles of a chloride, an acetate (an acetate compound), a sulfide, an iodide, a bromide, a peroxide, an oxide, a thiocyanate, or a mixture thereof. More preferably, the monovalent copper compound fine particles are particles of at least one selected from the group consisting of $CuCl$, $CuOOCCH_3$, $CuI$, $CuBr$, $Cu_2O$, $Cu_2S$, and $CuSCN$. Preferably, the iodide fine particles are particles of at least one selected from the group consisting of $CuI$, $AgI$, $SbI_3$, $IrI_4$, $GeI_2$, $GeI_4$, $SnI_2$, $SnI_4$, $TlI$, $PtI_2$, $PtI_4$, $PdI_2$, $BiI_3$, $AuI$, $AuI_3$, $FeI_2$, $CoI_2$, $NiI_2$, $ZnI_2$, $HgI$, and $InI_3$. More specifically, in the first embodiment, only one type of particles may be used as the held virus inactivating fine particles 2, or two or more types of particles may be held by the sheet body 1.

In the first embodiment, the virus inactivating fine particles 2 are fixed to the sheet body 1 through a binder. As described above, in FIG. 1, the silane monomer (or a polymerization product thereof) 3 is shown as the binder used. However, this is not a limitation, and any of the known binders may be used. No particular limitation is imposed on the binder so long as it has, for example, high adhesion to the sheet body 1. Examples of the usable binder include: synthetic resins such as polyester resins, amino resins, epoxy resins, polyurethane resins, acrylic resins, water-soluble resins, vinyl-based resins, fluorine resins, silicone resins, cellulose-based resins, phenolic resins, xylene resins, and toluene resins; and natural resins such as drying oils, for example, castor oil, linseed oil, and tung oil.

In the present embodiment, the silane monomer 3 or an oligomer obtained by polymerization of the silane monomer are used as the binder, as described above. This is because, since the molecular weights of these monomer and oligomer are low, the monomer or oligomer do not cover the virus inactivating fine particles 2 entirely, and the contact between the virus inactivating fine particles 2 and viruses adhering to the sheet body 1 is less likely to be prevented. Therefore, the use of the silane monomer (or a polymerization product thereof) 3 as the binder allows effective inactivation of viruses. Since the bonds provided by the silane monomer 3 are firm, the adhesion to the sheet body 1 is improved, and the virus inactivating fine particles 2 can be more stably supported on the sheet body 1.

Specific examples of the silane monomer used for the virus inactivating sheet 100 of the first embodiment include silane monomers represented by a general formula $X—Si(OR)_n$ (n is an integer of from 1 to 3). X is a functional group that reacts with an organic material, and examples thereof include a vinyl group, an epoxy group, a styryl group, a methacryl group, an acryloxy group, an isocyanate group, a polysulfide group, an amino group, a mercapto group, and a chloro group. Each OR is a hydrolyzable alkoxy group such as a methoxy group or an ethoxy group, and the three functional groups in the silane monomer may be the same or different. These alkoxy groups including methoxy and ethoxy groups are hydrolyzed to form silanol groups. The reactivity of such a silanol group, a vinyl group, an epoxy group, a styryl group, a methacryl group, an acryloxy group, an isocyanate group, and functional groups having an unsaturated bond and the like is known to be high. More specifically, in the virus inactivating sheet 100 of the first embodiment, the virus inactivating fine particles 2 are firmly held on the surface of the sheet body 1 by the chemical bonds 5 through the silane monomer having high reactivity.

Examples of the silane monomer represented by the above general formula include vinyltrichlorosilane, vinyltrimethoxysilane, vinyltriethoxysilane, vinyltriacetoxysilane, N-β-(N-vinylbenzylaminoethyl)-γ-aminopropyltrimethoxysilane, a hydrochloride of N-(vinylbenzyl)-2-aminoethyl-3-aminopropyltrimethoxysilane, 2-(3,4 epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, 3-isocyanatepropyltriethoxysilane, bis(triethoxysilylpropyl)tetrasulfide, 3-aminopropyltrimethoxysilane, 3-aminopropyltriethoxysilane, 3-triethoxysilyl-N-(1,3-dimethyl-butylidene)propylamine, N-phenyl-3-aminopropyltrimethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-mercaptopropylmethyldimethoxysilane, 3-mercaptopropyltrimethoxysilane, N-phenyl-3-aminopropyltrimethoxysilane, special aminosilanes, 3-ureidopropyltriethoxysilane, 3-chloropropyltrimethoxysilane, tetramethoxysilane, tetraethoxysilane, methyltrimethoxysilane, methyltriethoxysilane, dimethyldiethoxysilane, phenyltriethoxysilane, hexamethyldisilazane, hexyltrimethoxysilane, decyltrimethoxysilane, hydrolyzable group-containing siloxanes, fluoroalkyl group-containing oligomers, methylhydrogensiloxane, and silicone quaternary ammonium salt.

Examples of the silane-based oligomers include commercially available oligomers KC-89S, KR-500, X-40-9225, KR-217, KR-9218, KR-213, and KR-510, which are all products of Shin-Etsu Chemical Co., Ltd. These silane-based oligomers may be used alone, as a mixture of two or more thereof, or as a mixture with one or two or more of the above-described silane monomers.

As described above, in the virus inactivating sheet 100 of the first embodiment, the virus inactivating fine particles 2 are held by the sheet body 1 through the silane monomer or oligomer thereof 3 with at least part of their surfaces being exposed. Therefore, the probability of contact of viruses and bacteria adhering to the surface of the virus inactivating sheet 100 with the virus inactivating fine particles 2 can be made higher than that when the virus inactivating fine particles 2 are anchored to the sheet body 1 using a general binder such as a resin. Accordingly, the viruses can be effectively inactivated even by using a small amount of the virus inactivating fine particles 2.

Since the virus inactivating fine particles 2 are firmly fixed to the sheet body 1 by the chemical bonds 5 with the silane monomer or oligomer thereof 3, the amount of the virus inactivating fine particles 2 falling off the sheet body 1 is significantly reduced as compared to that when the particles are coated and fixed with, for example, a general binder component such as a resin. Therefore, the virus inactivating sheet 100 of the first embodiment can maintain its virus inactivating effect for a longer time. The virus inactivating fine particles 2 may be held not by the chemical bonds 5 but by a condensation reaction, amide bonds, hydrogen bonds, ion bonds, van der Waals forces, or physical adsorption. This can be achieved by selecting an appropriate silane monomer to be used.

In the first embodiment, no particular limitation is imposed on the form of holding the virus inactivating fine particles 2 by the sheet body 1, and the form may be appropriately selected by a person skilled in the art. For example, the virus inactivating fine particles 2 may be scattered on the sheet body 1. The virus inactivating fine particles 2 may be held as inorganic fine particle aggregates arranged two- or three-dimensionally. More specifically, the virus inactivating fine particles 2 may be held, for example, in a dot, island, or thin-film form. When the virus inactivating fine particles 2 are held as three-dimensional aggregates, they include particles bonded to the sheet body 1 through the silane monomer or oligomer thereof 3 (such particles are referred to as virus inactivating fine particles 2a) and particles bound to the sheet body 1 through at least the virus inactivating fine particles 2a.

Preferably, the virus inactivating fine particles 2 are held on the sheet body 1 as three-dimensional aggregates because a large number of fine irregularities are formed on the surface of the sheet body 1 and the adhesion of dust and the like to the sheet body 1 is suppressed by the irregularities. The suppression of the adhesion of dust and the like allows the virus inactivating effect of the virus inactivating sheet 100 to be maintained for a longer time.

In the virus inactivating sheet 100 of the first embodiment, a functional material is optionally used, in addition to the virus inactivating fine particles 2, to impart a desired function to the virus inactivating sheet 100. This functional material may be held on the surface of the sheet body 1. Examples of the functional material include other antiviral agents, antimicrobial agents, antifungal agents, anti-allergen agents, and catalysts. Such a functional material may be fixed to the sheet body 1, the virus inactivating fine particles 2, and the like through, for example, a general binder. As in the virus inactivating fine particles 2, the functional material may be held on the sheet body 1 by, for example, chemical bonds between the surface of the sheet body 1 and the silane monomer or oligomer thereof 3 bound to the surface of the functional material. Regardless of whether or not the functional material other than the virus inactivating fine particles 2 is held by the sheet body 1, the virus inactivating fine particles 2 may be fixed to the sheet body 1 through an additional reinforcing agent (hard coat agent) 4 in addition to the silane monomer or oligomer thereof 3, as shown in FIG. 1. In the following description, the materials held by the sheet body 1 (these materials include the virus inactivating fine particles 2, the silane monomer 3 (or oligomer thereof 3), and the like) are referred to a sheet-held composition.

A person skilled in the art can appropriately set the amount of the virus inactivating fine particles 2 held by the virus inactivating sheet 100 of the first embodiment, in consideration of the use purpose and application of the virus inactivating sheet 100 and of the size of the fine particles. The amount of the virus inactivating fine particles 2 in the sheet-held composition is preferably 0.1 percent by mass to 80.0 percent by mass and more preferably 0.1 percent by mass to 60.0 percent by mass. When the amount of the virus inactivating fine particles 2 is less than 0.1 percent by mass, the virus inactivating effect of the virus inactivating sheet 100 is lower than that when the amount falls within the above range. When the amount is larger than 80.0 percent by mass, the virus inactivating effect of the virus inactivating sheet 100 is not largely different from that when the amount falls within the above range. Further, the binding properties (the holding ability) of the oligomer formed by the condensation reaction of the silane monomer are reduced, and therefore the virus inactivating fine particles 2 fall off the sheet body 1 more easily than when the amount falls within the above range.

A description will next be given of the sheet body 1 on which the virus inactivating fine particles 2 are held. Any sheet body can be used as the sheet body 1 in the virus inactivating sheet 100 of the first embodiment, so long as the sheet body 1 can be chemically bound to the silane monomer or oligomer thereof 3 at at least part of the surface of the sheet body 1. Therefore, in the first embodiment, no particular limitation is imposed on the other properties of the sheet body. No particular limitation is imposed on the form of the sheet body 1, so long as it has a sheet shape. Examples of the sheet body 1 having a surface to which the silane monomer or oligomer thereof 3 can be chemically bound include a sheet body 1 having a surface that is at least partially composed of any of various resins, synthetic fibers, natural fibers such as cotton, hemp, and silk, and Japanese paper obtained from natural fibers.

When the surface or the entire part of the sheet body 1 is formed of a resin, a synthetic resin or a natural resin is used. Examples of such a resin include: thermoplastic resins such as polyethylene resins, polypropylene resins, polystyrene resins, ABS resins, AS resins, EVA resins, polymethylpentene resins, polyvinyl chloride resins, polyvinylidene chloride resins, polymethyl acrylate resins, polyvinyl acetate resins, polyamide resins, polyimide resins, polycarbonate resins, polyethylene terephthalate resins, polybutylene terephthalate resins, polyacetal resins, polyarylate resins, polysulfone resins, polyvinylidene fluoride resins, Vectran (registered trademark), and PTFE (polytetrafluoroethylene); biodegradable resins such as polylactic resins, polyhydroxybutyrate resins, modified starch resins, polycaprolactone resins, polybutylene succinate resins, polybutylene adipate terephthalate resins, polybutylene succinate terephthalate resins, and polyethylene succinate resins; thermosetting resins such as phenolic resins, urea resins, melamine resins, unsaturated polyester resins, diallyl phthalate resins, epoxy resins, epoxy acrylate resins, silicon resins, acrylic urethane resins, and urethane resins; elastomers such as silicone resins, polystyrene elastomers, polyethylene elastomers, polypropylene elastomers, and polyurethane elastomers; and natural resins such as lacquer.

In the first embodiment, the surface of the sheet body 1 may be formed of any of metal materials such as aluminum, stainless steel, and iron and inorganic materials such as glass and ceramics, so long as the chemical bonds 5 with the silane monomer or oligomer thereof 3 can be formed. In this case, as in the case of the resin substrate, for example, the unsaturated bond or reactive functional group of the silane monomer 3 may be reacted with the hydroxy group and the like on the surface of the metal through graft polymerization described later to form chemical bonds 5. In this manner, the virus inactivating fine particles 2 can be fixed to the metal sheet body 1. However, when functional groups that can form chemical bonds 5 are introduced to the surface of the sheet body 1 through a silane monomer, a titanium monomer, and the like, the virus inactivating fine particles 2 can be more firmly fixed. Examples of the functional group originating from the silane monomer and introduced to the surface of the sheet body 1 include a vinyl group, an epoxy group, a styryl group, a methacryl group, an acryloxy group, an isocyanate group, and a thiol group.

The sheet body 1 of the virus inactivating sheet 100 of the first embodiment will be described in more detail. For example, the sheet body 1 according to the first embodiment may be formed of fibers. More specifically, the sheet body 1 may be a sheet of woven fabric, knitted fabric, nonwoven fabric, and the like. Therefore, the virus inactivating sheet 100 of the first embodiment can be used to form masks, caps, shoe covers, filters for air conditioners, filters for air cleaners, filters for cleaners, filters for ventilation fans, filters for vehicles, filters for air-conditioning devices, filters for artificial ventilation, heat and moisture exchanger (HME), medical drapes (medical cover cloths and medical sheets), incise drapes, surgical tape, gauze, wallpaper, clothes, bedclothes, insecticidal nets, nets for chicken coops, and other nets such as mosquito nets.

Examples of the fibers constituting the sheet body 1 include fibers made of: polymer materials such as polyester, polyethylene, polypropylene, polyvinyl chloride, polyethylene terephthalate, polybutylene terephthalate, polytetramethylene terephthalate, nylon, acrylic, polytetrafluoroethylene, polyvinyl alcohol, Kevlar, polyacrylic acid, polymethyl methacrylate, rayon, cupra, Tencel, polynosic, acetate, triacetate, cotton, hemp, wool, silk, and bamboo; and metals such as aluminum, iron, stainless steel, brass, copper, tungsten, and titanium.

An additional member such as a film or a sheet may be stacked on the surface of the virus inactivating sheet 100 of the first embodiment. For example, waterproof properties can be imparted to the virus inactivating sheet 100 by stacking a waterproof film or sheet. With the virus inactivating sheet 100 having the waterproof properties, high-performance protective suits and medical gloves that can prevent permeation of viruses and blood can be produced by, for example, sewing the sheet, and bed sheets for hospitals and nursing care can also be produced.

A permeable film or sheet that allows no water to pass therethrough but allows air (moisture) to pass therethrough is preferably used as the film or sheet to be stacked so that the comfort of the user is ensured. More specifically, the film or sheet to be used can be selected from general commercially available products according to the use purpose.

An adhesive or the like may be staked on at least one principal surface of the virus inactivating sheet 100 of the first embodiment so that the user can freely and easily stick the sheet on a mask, a wall, or a floor. More specifically, by applying the virus inactivating sheet 100 of the first embodiment to the surface of an existing mask, a virus inactivating mask can be formed.

The sheet body 1 of the virus inactivating sheet 100 of the first embodiment is not limited to a breathable structural body and may not allow air to pass therethrough, i.e., may have air shielding properties. More specifically, the sheet body 1 may be formed into a film shape using any of: resins such as polyester, polyethylene, polyamide, polyvinyl chloride, polyvinylidene fluoride, polyvinyl alcohol, polyvinyl acetate, polyimide, polyamide imide, polytetrafluoroethylene, and a tetrafluoroethylene-ethylene copolymer; polymer sheets such as polycarbonate resin sheets and films, vinyl chloride sheets, fluorocarbon resin sheets, polyethylene sheets, silicone resin sheets, nylon sheets, ABS sheets, and urethane sheets; and metals such as titanium, aluminum, stainless steel, magnesium, and brass.

More preferably, the surface of the sheet body 1 having air-shielding properties is hydrophilized in advance by, for example, corona treatment, atmospheric plasma treatment, or flame treatment to improve the adhesion of the virus inactivating fine particles 2 to the sheet body 1. It is preferable for the sheet body 1 formed from a metal that rolling oil and corrosion products adhering to the surface thereof have been removed using a solvent, acid, alkali, and the like. The surface of the sheet body 1 may be coated or printed.

The virus inactivating sheet 100 which has air-shielding properties and has the virus inactivating fine particles 2 held thereon can be used in various fields such as wallpaper, curtains, blinds, desk mats, food storage bags, food wrapping films, keyboard covers, touch panels, touch panel covers, medical drapes, incise drapes, interior materials for hospital and other buildings, interior materials for trains and automobiles, sheets for vehicles, covers for chairs and sofas, facilities for handling viruses, soil-resistant sheets for doors and floor boards, masks for artificial respirators, and parts for artificial respirators.

The reinforcing material 4 is added when the virus inactivating fine particles 2 are firmly fixed to the sheet body 1, as described above. Any of the above-described various resins exemplified as the binder can be used as the reinforcing material 4. A silane monomer other than the compound used as the silane monomer 3 may be used as the reinforcing material 4.

The manufacture method of the virus inactivating sheet 100 of the first embodiment that has the virus inactivating fine particles 2 held thereon will next be described more specifically.

First, at least one material is selected from the above-described monovalent copper compounds and iodides. Then the selected material(s) is(are) pulverized into particles of the order of sub-micrometers to micrometers using, for example, a jet mill, a hammer mill, a ball mill, or a vibration mill to obtain virus inactivating fine particles. No particular limitation is imposed on the pulverization, and any of wet and dry processes can be used.

Next, the pulverized virus inactivating fine particles 2 are dispersed in a dispersion medium such as water, methanol, ethanol, MEK (methyl ethyl ketone), acetone, xylene, or toluene. If other materials such as the reinforcing material 4 and functional materials are mixed with the dispersion, these materials are added to the dispersion at this point. Then a dispersing agent such as a surfactant is added if necessary, and the resultant mixture is dispersed and pulverized using an apparatus such as a bead mill, a ball mill, a sand mill, a roll mill, a vibration mill, or a homogenizer. Then the silane monomer 3 is added to the dispersion to prepare a slurry containing the virus inactivating fine particles 2 dispersed therein. When the slurry is prepared in the manner described above, the diameter of the virus inactivating fine particles 2 is reduced, and these particles 2 are arranged on the surface of the sheet body 1 without excessively large gaps formed between the particles 2. The particle density of the virus inactivating fine particles 2 can thereby be increased, and accordingly, a high virus inactivating ability can be achieved.

The slurry prepared as described above is applied to the surface of the sheet body 1 using a method such as a dipping method, a spraying method, a roll coating method, a bar coating method, a spin coating method, a gravure printing method, an offset printing method, a screen printing method, or an inkjet printing method. If necessary, the solvent is removed by, for example, heating and drying. Next, the functional groups on the surface of the sheet body 1 are chemically bound to the silane monomer (the formation of the chemical bonds 5) through graft polymerization by re-heating or graft polymerization by irradiation with infrared rays, ultraviolet rays, an electron beam, or radioactive rays such as γ rays. During graft polymerization, the virus inactivating fine particles 2 are bound to each other through the silane monomer or formed oligomer thereof 3.

Next, if necessary, a film or an adhesive is stacked on the sheet body 1 using, for example, heating rollers to thereby obtain a virus inactivating sheet 100 of the first embodiment.

With the above-described virus inactivating sheet 100 of the first embodiment, various viruses can be inactivated regardless of the types of genomes and whether or not the viruses have an envelope. Examples of the viruses include rhinoviruses, polioviruses, foot and mouth disease viruses, rotaviruses, noroviruses, enteroviruses, hepatoviruses, astroviruses, sapoviruses, hepatitis E viruses, type A, B, and C influenza viruses, parainfluenza viruses, mumps viruses, measles viruses, human metapneumoviruses, RS viruses, Nipah viruses, Hendra viruses, yellow fever viruses, dengue viruses, Japanese encephalitis viruses, West Nile viruses, hepatitis B and C viruses, eastern and western equine encephalitis viruses, O'nyong-nyong viruses, rubella viruses, Lassa viruses, Junin viruses, Machupo viruses, Guanarito viruses, Sabia viruses, Crimean-Congo hemorrhagic fever viruses, sandfly fever, Hantaviruses, Sin Nombre viruses, rabies viruses, Ebola viruses, Marburg viruses, bat lyssaviruses, human T-lymphotropic viruses, human immunodeficiency viruses, human coronaviruses, SARS coronaviruses, human parvoviruses, polyoma viruses, human papilloma viruses, adenoviruses, herpes viruses, Varicella Zoster viruses, EB viruses, cytomegaloviruses, smallpox viruses, monkeypox viruses, cowpox viruses, molluscipox viruses, and parapoxviruses.

With the virus inactivating sheet 100 of the first embodiment, viruses can be inactivated even in the presence of, in addition to the viruses, lipids and proteins resulting from, for example, the adhesion of blood or droplets.

With the virus inactivating sheet 100 of the first embodiment, the viruses adhering thereto can be inactivated. Therefore, virus infection via the used sheet can be prevented, and the spread of viruses adhering to the sheet can be suppressed, so that the occurrence of secondary infection can be reduced.

Second Embodiment

Figure 2:
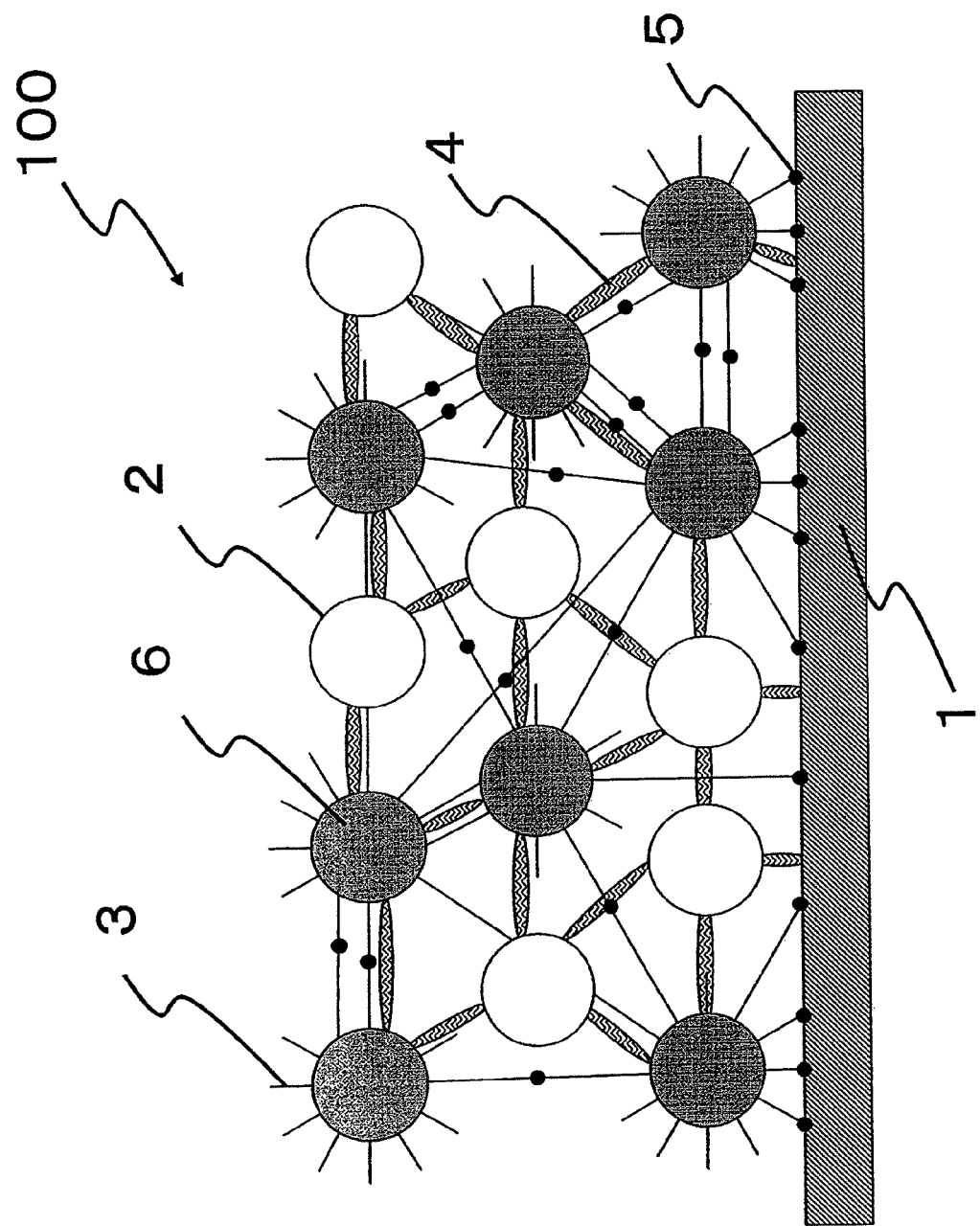
FIG. 2 is a schematic diagram of a cross-section of a virus inactivating sheet of a second embodiment.

A virus inactivating sheet 100 of a second embodiment will next be described. FIG. 2 is a schematic diagram of a cross-section of the virus inactivating sheet 100 of the second embodiment. The virus inactivating sheet 100 of the second embodiment has the same configuration as in the first embodiment except that, in addition to the virus inactivating fine particles 2 (hereinafter may be referred to as first inorganic fine particles), second inorganic fine particles 6 are held on the sheet body 1. In the second embodiment, the second inorganic fine particles 6 together with the first inorganic fine particles 2 form inorganic fine particle aggregates in which the inorganic fine particles are arranged two- or three-dimensionally. In other words, in the second embodiment, the inorganic particle aggregates containing the first inorganic fine particles 2 and the second inorganic fine particles 6 are held on the sheet body 1. In FIG. 2, a reinforcing material 4 is used to firmly fix the first inorganic fine particles 2 and the second inorganic fine particles 6 to the sheet body 1. However, as in the first embodiment, the reinforcing material 4 is not necessarily included. Structures common to those in the first embodiment are denoted by the same reference numerals, and the description will be omitted.

The second inorganic fine particles 6 form chemical bonds 5 with the sheet body 1 through a silane monomer or oligomer thereof 3 and also form chemical bonds 5 with each other through the silane monomer or oligomer thereof 3. Therefore, in the second embodiment, the first inorganic fine particles 2 serving as virus inactivating fine particles are held on the sheet body 1 through the silane monomer or oligomer thereof 3 and through the second inorganic fine particles 6. In the second embodiment, the first inorganic fine particles 2 are held on the sheet body 1 so as to be entangled with groups of the second inorganic fine particles 6 forming chemical bonds 5 with each other through the silane monomer or oligomer thereof 3. Therefore, the first inorganic fine particles 2 are prevented from falling off the sheet body 1 not only by the chemical bonds 5 but also physically. In the virus inactivating sheet 100 of the second embodiment, the virus inactivating fine particles 2 are more effectively prevented from falling off as compared to those in the virus inactivating sheet 100 of the first embodiment. Therefore, the virus inactivating ability and disinfectant ability can be maintained for a longer time.

In the second embodiment, the groups of the second inorganic fine particles 6 that form the chemical bonds 5 with each other through the silane monomer 3 prevent the first inorganic fine particles 2 from falling off the sheet body 1. Therefore, the first inorganic fine particles 2 may not form bonds with the second inorganic fine particles 6 and the sheet body 1 through the silane monomer or oligomer thereof 3.

In the virus inactivating sheet 100 of the second embodiment, the first inorganic fine particles 2 serving as the virus inactivating fine particles are bound to the second inorganic fine particles 6 and the sheet body 1 through the silane monomer and oligomer thereof 3, and accordingly, the surfaces of the first inorganic fine particles 2 are exposed, as in the first embodiment. Therefore, the probability of contact of viruses adhering to the surface of the virus inactivating sheet 100 with the virus inactivating fine particles 2 can be made higher than that when the virus inactivating fine particles 2 are fixed to the sheet body 1 using, for example, a general binder, so that the viruses can be effectively inactivated even by using a small amount of the virus inactivating fine particles 2.

No particular limitation is imposed on the second inorganic fine particles 6 according to the second embodiment, so long as they can be bound to the silane monomer or oligomer thereof 3, and a person skilled in the art can select appropriate second inorganic fine particles 6. Specifically, nonmetal oxides, metal oxides, metal composite oxides, nitrides, carbides, silicates, and mixtures thereof can be used. The second inorganic fine particles 6 may be amorphous or crystalline. Examples of the nonmetal oxides include silicon oxide. Examples of the metal oxides include magnesium oxide, barium oxide, barium peroxide, aluminum oxide, tin oxide, titanium oxide, zinc oxide, titanium peroxide, zirconium oxide, iron oxide, iron hydroxide, tungsten oxide, bismuth oxide, indium oxide, gibbsite, boehmite, diaspore, antimony oxide, cobalt oxide, niobium oxide, manganese oxide, nickel oxide, cerium oxide, yttrium oxide, and praseodymium oxide. Examples of the metal composite oxides include barium titanium oxide, cobalt aluminum oxide, zirconium lead oxide, niobium lead oxide, $TiO_2$—$WO_3$, $AlO_3$—$SiO_2$, $WO_3$—$ZrO_2$, $WO_3$—$SnO_2$, $CeO_2$—$ZrO_2$, In—Sn, Sb—Sn, Sb—Zn, In—Sn—Zn, $B_2O_3$—$SiO_2$, $P_2O_5$—$SiO_2$, $TiO_2$—$SiO_2$, $ZrO_2$—$SiO_2$, $Al_2O_3$—$TiO_2$, $Al_2O_3$—$ZrO_2$, $Al_2O_3$—$CaO$, $Al_2O_3$—$B_2O_3$, $Al_2O_3$—$P_2O_5$, $Al_2O_3$—$CeO_2$, $Al_2O_3$—$Fe_2O_3$, $TiO_2$—$ZrO_2$, $TiO_2$—$ZrO_2$—$SiO_2$, $TiO_2$—$ZrO_2$—$Al_2O_3$, $TiO_2$—$Al_2O_3$—$SiO_2$, and $TiO_2$—$CeO_2$—$SiO_2$. Examples of the nitrides include titanium nitride, tantalum nitride, and niobium nitride. Examples of the carbides include silicon carbide, titanium carbide, and niobium carbide. Examples of the adsorptive silicates include: synthetic zeolites such as zeolite A, zeolite P, zeolite X, and zeolite Y; natural zeolites such as clinoptilolite, sepiolite, and mordenite; layer silicate compounds such as kaolinite, montmorillonite, Japanese acid clay, and diatomaceous earth; and cyclosilicate compounds such as wollastonite and neptunite. Other examples include phosphate compounds such as tricalcium phosphate, calcium hydrogen phosphate, calcium pyrophosphate, calcium metaphosphate, and hydroxyapatite, activated carbon, and porous glass.

A person skilled in the art can appropriately set the diameter of the second inorganic fine particles 6, according to, for example, the use purpose and application of the sheet and the diameter of the first inorganic fine particles 2. In consideration of the bonding strength to the sheet body 1, the diameter of the second inorganic fine particles 6 is preferably 500 nm or smaller and more preferably 300 nm or smaller. As described above, a person skilled in the art can appropriately set the diameter of the second inorganic fine particles 6. However, when the diameter is smaller than 1 nm, the particles are physically unstable and coagulate with each other, as in the case of the first inorganic fine particles 2, and it is difficult to support the particles on the sheet body 1 uniformly. Therefore, the diameter is preferably 1 nm or larger.

The manufacture method of the virus inactivating sheet 100 of the second embodiment that has the first inorganic fine particles 2 held thereon will next be described more specifically.

First, as in the first embodiment, at least one material is selected from the monovalent copper compounds and iodides. Then the selected material(s) is(are) pulverized into particles of the order of micrometers using, for example, a jet mill, a hammer mill, a ball mill, or a vibration mill to obtain virus inactivating fine particles 2 (first inorganic fine particles 2). No particular limitation is imposed on the pulverization, and any of wet and dry processes can be used.

Next, the pulverized virus inactivating fine particles 2 are mixed with the second inorganic fine particles 6 to which the silane monomer 3 has been bound through dehydration condensation, and the mixture is dispersed in a dispersion medium such as water, methanol, ethanol, MEK, acetone, xylene, or toluene. If, in addition to the virus inactivating fine particles 2 and the second inorganic fine particles 6 to which the silane monomer 3 has been bonded, other materials such as the reinforcing material 4 and functional materials are mixed with the dispersion, these materials are added to the dispersion at this point. Then a dispersing agent such as a surfactant is added if necessary, and the resultant mixture is dispersed and pulverized using an apparatus such as a bead mill, a ball mill, a sand mill, a roll mill, a vibration mill, or a homogenizer to prepare a slurry containing the virus inactivating fine particles 2 and the second inorganic fine particles 6 dispersed therein. When the slurry is prepared in the manner described above, the diameters of the virus inactivating fine particles 2 and the second inorganic fine particles 6 are reduced, and the first virus inactivating fine particles 2 and the second inorganic fine particles 6 are arranged on the surface of the sheet body 1 without excessively large gaps formed between the particles 2 and 6. The particle density of the virus inactivating fine particles 2 can thereby be increased, and the groups of the second inorganic fine particles 6 can be more firmly fixed to the surface of the sheet body 1. Therefore, a high virus inactivating ability and a high disinfectant ability can be achieved, and the virus inactivating ability and disinfectant ability can be maintained for a longer time.

The chemical bonds between the second inorganic fine particles 6 and the silane monomer can be formed by an ordinary method. In one exemplary method, the silane monomer 3 is added to a dispersion of the second inorganic fine particles 6, and the resultant dispersion is heated under reflux to allow the silane monomer 3 to be bonded to the surfaces of the particles 6 through a dehydration-condensation reaction to thereby form thin films made of the silane monomer 3. In another exemplary method, the silane monomer 3 is added to a dispersion of the second inorganic fine particles 6 that has been subjected to pulverization to reduce the size of the particles, or alternatively, the silane monomer 3 is added to a dispersion of the second inorganic fine particles 6, and the resultant dispersion is subjected to pulverization to reduce the size of the particles. Then the solid and liquid are separated from the dispersion including the silane monomer 3, and the separated solid is heated at 100° C. to 180° C. to allow the silane monomer to be bound to the surfaces of the second inorganic fine particles 6 through a dehydration-condensation reaction. The resultant particles are pulverized and then re-dispersed.

In the methods described above, the amount of the silane monomer 3 to be added to the dispersion depends on the average particle diameter and material of the second inorganic fine particles 6. However, when the amount is 3 percent by mass to 30 percent by mass based on the mass of the second inorganic fine particles 6, the mutual binding strength between the second inorganic fine particles 6 and the binding strength between the groups of the second inorganic fine particles 6 and the sheet body 1 constituting the virus inactivating sheet 100 of the present invention do not cause any practical problems. Even after the silane monomer 3 and the like are bound to the first inorganic fine particles 2 and the second inorganic fine particles 6, the surfaces of the first inorganic fine particles 2 are exposed sufficiently. In addition, an excess of silane monomer that is not involved in the bonding may be present.

The description of the method of manufacturing the virus inactivating sheet 100 of the second embodiment will be continued. As in the first embodiment, the above-prepared slurry is applied to the surface of the sheet body 1 using a method such as a dipping method, a spraying method, a roll coating method, a bar coating method, a spin coating method, a gravure printing method, an offset printing method, a screen printing method, or an inkjet printing method. If necessary, the solvent is removed by heating and drying and the like. Next, the functional groups on the surface of the sheet body 1 are chemically bound, through graft polymerization by re-heating or graft polymerization by irradiation with infrared rays, ultraviolet rays, an electron beam, or radioactive rays such as γ rays, to the silane monomer 3 bonded to the surfaces of the second inorganic fine particles 6 which face the surface of the sheet body 1 (the formation of the chemical bonds 5). At the same time, the silane monomers 3 on the surfaces of the second inorganic fine particles 6 are chemically bound to each other to form an oligomer. At the same time, the virus inactivating fine particles 2 are bonded to the second inorganic fine particles 6 through the silane monomer 3. If an additional silane monomer serving as the reinforcing material 4 is added to obtain more firm bonds between the second inorganic fine particles 6 and the sheet body 1, the virus inactivating fine particles 2 are bound to the second inorganic fine particles 6 and the sheet body 1 through the additional silane monomer added as the reinforcing material 4 and the oligomer 3 resulting from the silane monomer 3. Through the above process, the virus inactivating fine particles 2 (the first inorganic fine particles 2) having a virus inactivating ability are surrounded by the groups of the second inorganic fine particles 6 and held by the sheet body 1. If necessary, of ter the sheet body 1 having the virus inactivating fine particles 2 held on the surface thereof is obtained as described above, a film or an adhesive is stacked in the same manner as in the first embodiment to obtain the virus inactivating sheet 100 of the second embodiment.

In the above description, the silane monomer 3 is bound to the second inorganic fine particles 6 in advance, but this mode is not a limitation. The virus inactivating fine particles 2, second inorganic fine particles 6 to which no silane monomer has been bound, and the silane monomer 3 may be dispersed in a dispersion medium. A person skilled in the art may appropriately set the amount of the silane monomer 3 added. As in the above description, the amount added may be, for example, 3 percent by mass to 30 percent by mass based on the mass of the second inorganic fine particles 6. In the above range of addition, the mutual binding strength between the second inorganic fine particles 6 and the binding strength between the groups of the second inorganic fine particles 6 and the sheet body 1 do not cause any practical problems. Even after the silane monomer 3 is bound to the second inorganic fine particles 6, the surfaces of the first inorganic fine particles 2 are exposed sufficiently.

Third Embodiment

A virus inactivating sheet 100 of a third embodiment of the present invention will next be described with reference to FIG. 3.

Figure 3:
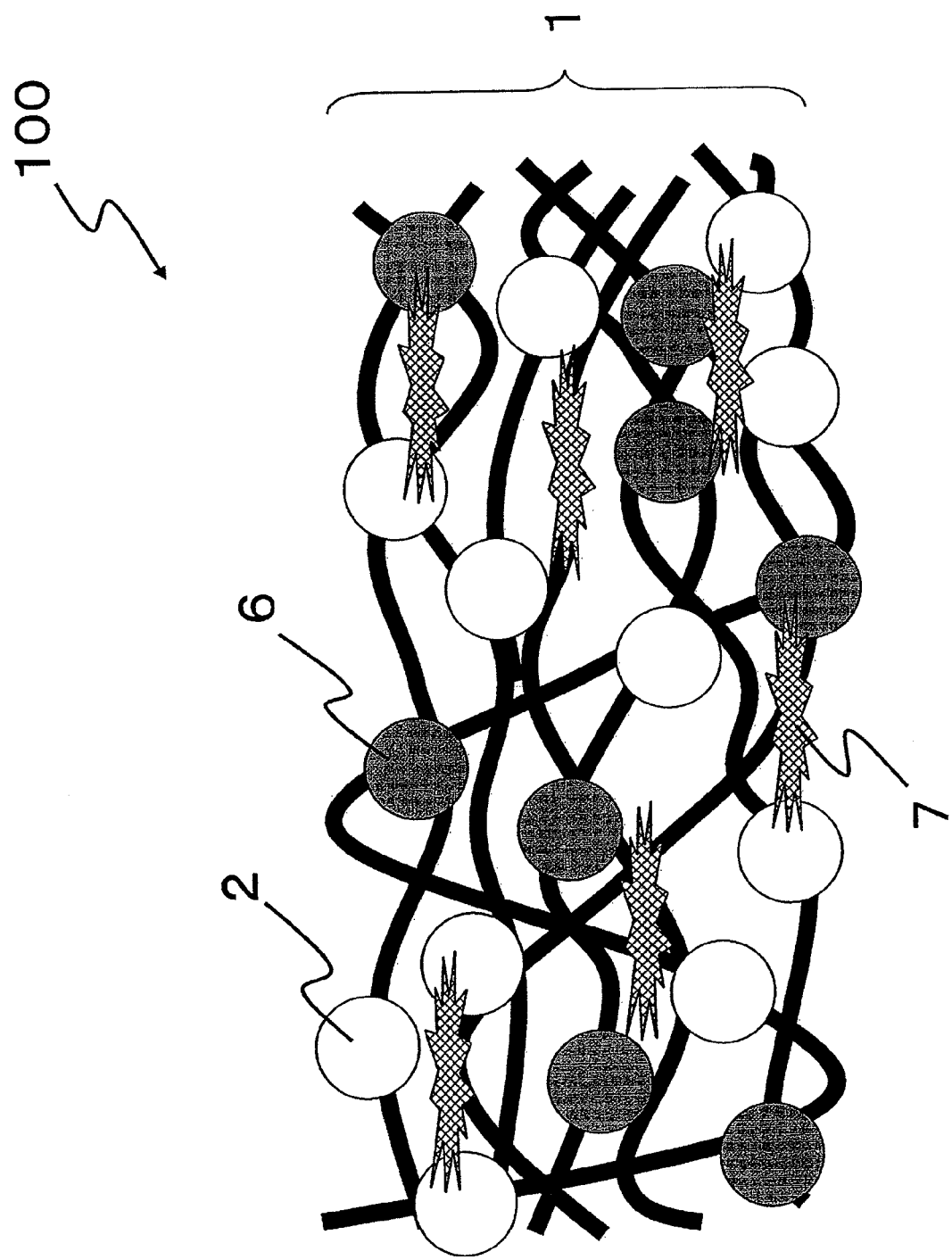
FIG. 3 is a schematic diagram of a cross-section of a virus inactivating sheet of a third embodiment.

FIG. 3 is an enlarged schematic view of apart of a cross-section of the virus inactivating sheet 100 of the third embodiment of the present invention. In the virus inactivating sheet 100 of the third embodiment, virus inactivating fine particles 2 having a virus inactivating ability are fixed inside a sheet body 1.

In the configuration of the third embodiment, only the virus inactivating fine particles 2 may be held, or other inorganic fine particles 6 and the like that are not virus inactivating fine particles may also be held, as in, for example, the second embodiment. FIG. 3 schematically shows an example in which the virus inactivating fine particles 2 and one type of inorganic fine particles 6 different from the virus inactivating fine particles 2 are held. In another possible configuration, two or more types of inorganic fine particles may be held, in addition to the virus inactivating fine particles 2.

No particular limitation is imposed on the size of the virus inactivating fine particles 2 contained. However, the average particle diameter is preferably 3,000 min or smaller. In consideration of the fact that the virus inactivating fine particles 2 can fall off the inside of the sheet body 1 in some use environments and with the passage of time, the average particle diameter is particularly preferably 1 nm to 1,000 μm.

The virus inactivating fine particles 2 of the third embodiment can be held in the internal space of the sheet 1 by mixing the particles with, for example, a nonwoven fabric produced by entangling fibers or mixed-paper produced by mixing pulp with a binder when the nonwoven fabric or the mixes-paper and the like is produced as the sheet body 1.

Examples of the fibers forming the nonwoven fabric include, in addition to the above-described synthetic fibers and natural fibers such as cotton, hemp, and silk, glass, metals, ceramics, pulp, and carbon fibers. The nonwoven fabric is produced in two steps. First, a piled layer referred to as fleece and used as the base of the nonwoven fabric is produced. Then the fibers in the fleece are bonded to each other, and layers of the fleece are stacked on top of each other. In addition, the virus inactivating fine particles 2 of the third embodiment may be mixed with the fibers when the fleece is formed or when the fleece layers are stacked. When layers of the fleece are stacked, a fleece layer containing the virus inactivating fine particles 2 and a fleece layer containing no virus inactivating fine particles 2 may be stacked.

Any of the common manufacturing methods such as a dry method, a wet method, a spun bonding method, and a melt blowing method can be used as the method of manufacturing the fleece. In consideration of the stability of the virus inactivating fine particles 2, a dry method in which no water is used and heating is not performed is preferably used.

Any of the common manufacturing methods such as a thermal bonding method, a chemical bonding method, a needle punching method, a spun lace method, a stitch bonding method, and a steam jet method can be used as the method of bonding the fleece.

An adhesive resin 7 may be mixed to improve the binding strength within the fleece. Specific examples of the adhesive resin 7 include saturated polyester resins, unsaturated polyester resins, polyvinyl alcohol, polyvinyl acetate, urethane resins, epoxy resins, acrylic resins, alkyd resins, and starch pastes.

When mixed-paper is used as the sheet body 1 of the virus inactivating sheet 100 of the third embodiment, the mixed-paper is obtained by subjecting pulp to paper making. Any of various pulps such as wood pulp, polyethylene pulp, rayon pulp, and vinylon pulp may be used as the above pulp. A single type or a combination of a plurality of types of organic synthetic fibers such as polyester-based fibers, polyurethane-based fibers, polyamide-based fibers, polyvinyl alcohol-based fibers, polyvinyl chloride-based fibers, polyolefin-based fibers, and polyacrylonitrile-based fibers may be used in addition to the pulp.

In the paper making, for example, an appropriate amount of a reinforcing agent such as glass fibers or milled fibers is added to the pulp for the purpose of ensuring the strength as a structural body. The mixture is mixed with water to prepare a diluted slurry, and then the diluted slurry is strained using a paper machine such as a cylinder paper machine. The virus inactivating fine particles 2 of the third embodiment are added to the unstrained slurry and are thereby anchored inside the sheet body 1.

The virus inactivating sheets of the first to third embodiments have been described, but the present invention is not limited thereto. Other embodiments are, of course, possible. For example, in the first and second embodiments, the virus inactivating fine particles 2 are held on the surface of the sheet body 1, but this is not a limitation. The virus inactivating fine particles 2 may be held in the whole sheet. For example, the virus inactivating fine particles 2 may be held so as to be surrounded by the fibers constituting the sheet 1. It is easy for a person skilled in the art to understand that, depending on the constituent material of the sheet body 1 and the manufacturing method used, the virus inactivating fine particles 2 can be held not only on the surface of the sheet but also inside the sheet, even in the first and second embodiments.

The present invention will next be specifically described by way of Examples. However, the present invention is not limited only to these Examples.

EXAMPLES

Evaluation of Antiviral Ability by Hemagglutination Reaction

The antiviral ability of each of materials (Reference Examples 1 to 27) was evaluated. An influenza virus (influenza A/Kitakyusyu/159/93(H3N2)) cultured in MDCK cells was used as a subject virus. The titer (HA titer) in the hemagglutination reaction (HA) of the influenza virus that had been brought into contact with one of the above materials was determined by the routine method.

More specifically, a two-fold dilution series of a sample solution that had been brought into contact with a suspension of one of the above materials was prepared in phosphate buffered saline (PBS), and 50 μL of the prepared solutions were added to the wells of a plastic-made 96 round-bottom well plate. Then 50 μL of a 0.5 vol % chicken erythrocyte suspension was added to each of the wells, and the wells were allowed to stand at 4° C. for 60 minutes. Then the state of sedimentation of the erythrocyte was visually observed. The HA titer was determined as the maximum dilution factor of the virus solution at which the sedimentation of the erythrocyte was not found.

The sample solutions were obtained as follows. First, one of the materials in the Reference Examples shown in Table 1 was suspended in PBS at 10 percent by mass and 1 percent by mass to prepare samples. Then 450 μL of an influenza virus solution with an HA titer of 256 was added to 450 μL of the prepared samples with two different concentrations, and the resultant solutions were allowed to react at room temperature for 10 minutes under stirring using a micro-tube rotator. The concentration of the material in each solution was 5 percent by mass or 0.5 percent by mass. A sample prepared by adding 450 μL of the virus solution with an HA titer of 256 to 450 μL of PBS and stirring the mixture for 10 minutes using a micro-tube rotator was used as a control. In the present description, the concentration of a suspension means the percent by mass of a specific component (for example, an iodide or a monovalent copper compound) based on the total mass (100%) of the components constituting the suspension including an iodide or a monovalent copper compound and a solvent. Then the solid content was precipitated by centrifugation, and the supernatant was collected and used as a sample solution. The results of the measurement of the HA titer of each sample solution are shown in Table 2.

TABLE 1

| REFERANCE EXAMPLE NO. | MATERIAL NAME | MOLECULAR FORMULA | MANUFACTURER (PURCHASED FROM) | QUALITY-GRADE |
|---|---|---|---|---|
| 1 | COPPER(I) IODIDE | CuI | WAKO | WAKO 1ST GRADE |
| 2 | SILVER(I) IODIDE | AgI | WAKO | CHEMICAL USE |
| 3 | ANTIMONY(III) IODIDE | $SbI_3$ | Strem chemicals (WAKO) | 99.90% |
| 4 | IRIDIUM(IV) IODIDE | $IrI_4$ | Alfa Aesar (WAKO) | 99.95% |
| 5 | GERMANIUM(IV) IODIDE | $GeI_4$ | Alfa Aesar (WAKO) | 99.999% |
| 6 | GERMANIUM(II) IODIDE | $GeI_2$ | AIDRICH | 99.99% |
| 7 | TIN(II) IODIDE | $SnI_2$ | Alfa Aesar (WAKO) | 99+% |
| 8 | TIN(IV) IODIDE | $SnI_4$ | Strem chemicals (WAKO) | 95% |
| 9 | THALLIUM(I) IODIDE | TlI | WAKO | OPTICAL USE |
| 10 | PLATINUM(II) IODIDE | $PtI_2$ | Strem chemicals (WAKO) | 99% |
| 11 | PLATINUM(IV) IODIDE | $PtI_4$ | Alfa Aesar (WAKO) | 99.95% |
| 12 | PALLADIUM(II) IODIDE | $PdI_2$ | Strem Chemicals, Inc. | |
| 13 | BISMUTH(III) IODIDE | $BiI_3$ | Strem chemicals (WAKO) | 99.999% |
| 14 | GOLD(I) IODIDE | AuI | Strem chemicals (WAKO) | (WAKO) 99% |
| 15 | GOLD(III) IODIDE | $AuI_3$ | ChemPur Feinchemikalien und Forschungsbedarf GmbH (WAKO) | |
| 16 | IRON(II) IODIDE | $FeI_2$ | Aldrich | >99.99% |
| 17 | COBALT(II) IODIDE | $CoI_2$ | Aldrich | 95% |
| 18 | NICKEL(II) IODIDE | $NiI_2$ | Alfa Aesar (WAKO) | 99.50% |
| 19 | ZINC(II) IODIDE | $ZnI_2$ | WAKO | WAKO 1ST GRADE |
| 20 | MERCURY(I) IODIDE | HgI | WAKO | CHEMICAL USE |
| 21 | INDIUM(III) IODIDE | $InI_3$ | Alfa Aesar (WAKO) | 99.999% |
| 22 | COPPER(I) CHLORIDE | CuCl | WAKO | SPECIAL GRADE REAGENT |
| 23 | COPPER(I) BROMIDE | CuBr | WAKO | WAKO 1ST GRADE |
| 24 | COPPER(I) ACETATE | $CuOOCCH_3$ | TOKYO CHEMICAL INDUSTRY CO., LTD. | REAGENT 98% |
| 25 | COPPER(I) THIOCYANATE | CuSCN | WAKO | CHEMICAL USE |
| 26 | COPPER(I) SULFIDE | $Cu_2S$ | Alfa Aesar (WAKO) | 99.5% |
| 27 | COPPER(I) OXIDE | $Cu_2O$ | WAKO | 99.5+% |

NOTE: "WAKO" IN TABLE MEANS "WAKO PURE CHEMICAL INDUSTRIES, LTD."

TABLE 2

| REFERANCE EXAMPLE NO. | MATERIAL NAME | MOLECULAR FORMULA | HA TITER MATERIAL CONCENTRATION (PERCENT BY MASS) 5 | 0.5 |
|---|---|---|---|---|
| 1 | COPPER(I) IODIDE | CuI | 8 | 32 |
| 2 | SILVER(I) IODIDE | AgI | 32 | 64 |
| 3 | ANTIMONY(III) IODIDE | $SbI_3$ | 16 | 32 |
| 4 | IRIDIUM(V) IODIDE | $IrI_4$ | 32 | 64 |
| 5 | GERMANIUM(IV) IODIDE | $GeI_4$ | <2 | <2 |
| 6 | GERMANIUM(II) IODIDE | $GeI_2$ | <2 | 2 |
| 7 | TIN(II) IODIDE | $SnI_2$ | <2 | 2 |
| 8 | TIN(IV) IODIDE | $SnI_4$ | <2 | 2 |
| 9 | THALLIUM(I) IODIDE | TlI | 32 | 64 |
| 10 | PLATINUM(I) IODIDE | $PtI_2$ | <2 | 64 |
| 11 | PLATINUM(IV) IODIDE | $PtI_4$ | 32 | 64 |
| 12 | PALLADIUM(II) IODIDE | $PdI_2$ | 2 | 64 |
| 13 | BISMUTH(III) IODIDE | $BiI_3$ | 8 | 64 |
| 14 | GOLD(I) IODIDE | AuI | 4 | 64 |
| 15 | GOLD(III) IODIDE | $AuI_3$ | 8 | 64 |
| 16 | IRON(II) IODIDE | $FeI_2$ | <2 | <2 |
| 17 | COBALT(II) IODIDE | $CoI_2$ | <2 | 8 |
| 18 | NICKEL(II) IODIDE | $NiI_2$ | <2 | 4 |
| 19 | ZINC(II) IODIDE | $ZnI_2$ | <2 | 4 |
| 20 | MERCURY(I) IODIDE | HgI | 32 | 64 |
| 21 | INDIUM(III) IODIDE | $InI_3$ | <2 | <2 |
| 22 | COPPER(I) CHLORIDE | CuCl | <2 | <2 |
| 23 | COPPER(I) BROMIDE | CuBr | <2 | 32 |
| 24 | COPPER(I) ACETATE | $CuOOCCH_3$ | <2 | <2 |

TABLE 2-continued

| REFERANCE EXAMPLE NO. | MATERIAL NAME | MOLECULAR FORMULA | HA TITER MATERIAL CONCENTRATION (PERCENT BY MASS) 5 | 0.5 |
|---|---|---|---|---|
| 25 | COPPER(I) THIOCYANATE | CuSCN | 16 | 64 |
| 26 | COPPER(I) SULFIDE | $Cu_2S$ | 16 | 64 |
| 27 | COPPER(I) OXIDE | $Cu_2O$ | 8 | 64 |
| CONTROL | (PHOSPHATE BUFFERED SALINE) | | 128 | |

NOTE 1: "<2" IN TABLE REPRESENTS "EQUAL TO OR LOWER THAN THE LOWER LIMIT OF THE HA TITER MEASUREMENT"
NOTE 2: THE TEST FOR THE CONTROL WAS PERFORMED AT A MATERIAL CONCENTRATION OF 0% (ONLY PHOSPHATE BUFFERED SALINE)

As can be seen from the results in Table 2, all the materials in Reference Examples 1 to 27 were found to have a virus inactivating effect. When the concentration was 5%, the HA titer was 32 or lower, i.e., 75% or more of the virus was found to be inactivated. Particularly, for each of the materials including $GeI_4$, $GeI_2$, $SnI_2$, $SnI_4$, $PtI_2$, $FeI_2$, $CoI_2$, $NiI_2$, $ZnI_2$, $InI_3$, CuCl, CuBr, and $CuOOCCH_3$, a high effect, i.e., inactivation of 98.44% or more of the virus, which is the lower limit of the measurement of the HA titer in this test, was found.

Preparation of Virus Inactivating Sheets

Example 1

A powder of copper (I) iodide in Reference Example 1 was used as fine particles having a virus inactivating ability. Methacryloxypropyltrimethoxy silane (KBM-503, product of Shin-Etsu Chemical Co., Ltd.), which is a silane monomer having an unsaturated bond, was subjected to dehydration-condensation by an ordinary method to covalently-bond the silane to the surfaces of zirconium oxide particles (PCS, product of Nippon Denko Co., Ltd.), and the resultant particles were used as second inorganic fine particles. 40 g of the powder of copper (I) iodide and 60 g of the second inorganic fine particles were pre-dispersed in 900.0 g of ethanol, and these particles were pulverized and dispersed using a bead mill to obtain a particle dispersion. The average particle diameter of the obtained particle dispersion was 105 nm. The average particle diameter as used herein is a volume average particle diameter. Ethanol was added to the obtained particle dispersion to adjust the concentration of the solid to 1 percent by mass. Then tetramethoxy silane (KBM-04, product of Shin-Etsu Chemical Co., Ltd.) was added in an amount of 0.3 percent by mass to obtain a coating solution.

Then a rayon nonwoven fabric (product of KURARAYKURAFLEX Co., Ltd.) of 18 $g/m^2$ was impregnated with the above coating solution and dried to obtain a virus inactivating nonwoven sheet having a virus inactivating effect.

Example 2

A polyester monofilament mesh (product of NBC Meshtec Inc.) of 305 mesh was dipped in the coating solution prepared in Example 1. Any excess of the solution was removed, and the resultant mesh was dried at 110° C. for 1 minute. Then the mesh was irradiated with an electron beam at an acceleration voltage of 200 kV and 50 kGy to obtain a virus inactivating mesh sheet having a virus inactivating effect.

Example 3

A powder of copper(I) iodide in Reference Example 1 was used as fine particles having a virus inactivating ability and was pulverized using a dry pulverizer, Nano Jetmizer (product of Aishin Nano Technologies CO., Ltd.). The average particle diameter was 170 nm.

SHC900 (a mixture of melamine resin, silicone resin, and alkyd resin, product of Momentive Materials Japan LLC) was added to isopropanol such that the amount of the solid was 5 percent by mass. The powder of copper(I) iodide pulverized using the jet mill was added to the prepared mixture (a mixture of SHC900 and isopropanol) in an amount of 1 percent by mass, and the resultant mixture was stirred using a homogenizer to prepare a coating solution.

Then a rayon nonwoven fabric (product of KURARAYKURAFLEX Co., Ltd.) of 18 $g/m^2$ was dipped with the above coating solution and dried at 100° C. to cure the coating, and a virus inactivating nonwoven sheet having a virus inactivating effect was thereby obtained.

Example 4

A polyester film (product of TORAY Industries, Inc.) having a thickness of 125 μm was hydrophilized by corona treatment and was coated with the coating solution prepared in Example 1 using a bar coater. The resultant film was dried at room temperature to obtain a virus inactivating film sheet having a virus inactivating effect.

Example 5

The powder of copper(I) iodide pulverized by the jet mill in Example 3 was added to ethanol in an amount of 2.0 percent by mass, and tetramethoxy silane (KBM-04, product of Shin-Etsu Chemical Co., Ltd.) was added to the mixture (the powder of copper(I) iodide and ethanol) in an amount of 0.4 percent by mass. The mixture was pre-dispersed using a homogenizer for 5 minutes to prepare a slurry.

A rayon nonwoven fabric (product of SHINWA Corp.) of 20 $g/m^2$ was dipped in the prepared slurry. Any excess of the slurry was removed, and the nonwoven fabric was dried at 120° C. for 10 minutes to obtain a virus inactivating nonwoven sheet having a virus inactivating effect.

Example 6

A powder of silver(I) iodide in Reference Example 2 was used as fine particles having a virus inactivating ability and was pulverized into an average particle diameter of 140 nm using a dry pulverizer, Nano Jetmizer (product of Aishin Nano Technologies CO., Ltd.). The pulverized silver(I) iodide fine particles were added to ethanol in an amount of 4.0 percent by mass, and tetramethoxy silane (KBM-04 product of Shin-Etsu Chemical Co., Ltd.) was added to the mixture in an amount of 0.4 percent by mass. The mixture was pre-dispersed using a homogenizer for 5 minutes to prepare a slurry. The average particle diameter as used herein is a volume average particle diameter.

Next, a cotton nonwoven fabric of 80 g/m² was dipped in the prepared slurry. Any excess of the slurry was removed, and the nonwoven fabric was dried at 120° C. for 10 minutes to obtain a wiping sheet having a virus inactivating effect.

Example 7

A powder of silver(I) iodide in Reference Example 2 was used as fine particles having a virus inactivating ability. Methacryloxypropyltrimethoxy silane (KBM-503, product of Shin-Etsu Chemical Co., Ltd.), a silane monomer having an unsaturated bond, was subjected to dehydration-condensation by an ordinary method to covalently-bond the silane to the surfaces of zirconium oxide particles (product of Nippon Denko Co., Ltd.), and the resultant particles were used as inorganic fine particles other than the virus inactivating fine particles. 40 g of the powder of silver(I) iodide and 60 g of the inorganic fine particles were pre-dispersed in 900.0 g of methanol, and these particles were pulverized and dispersed using a bead mill to obtain a particle dispersion. The average particle diameter of the obtained particle dispersion (slurry) was 140 nm. Ethanol was added to the obtained slurry to adjust the concentration of the solid to 0.5 percent by mass. The average particle diameter as used herein is a volume average particle diameter.

Then the above slurry was applied to a rayon nonwoven fabric of 80 g/m² by spraying, and the nonwoven fabric was dried to obtain a wiping sheet having a virus inactivating effect.

Example 8

A powder of copper(I) thiocyanate in Reference Example 25 was used as fine particles having a virus inactivating ability and was pulverized into an average particle diameter of 120 nm using a dry pulverizer, Nano Jetmizer (product of Aishin Nano Technologies CO., Ltd.). The pulverized copper(I) thiocyanate fine particles were added to ethanol in an amount of 4.0 percent by mass, and tetramethoxy silane (KBM-04, product of Shin-Etsu Chemical Co., Ltd.) was further added in an amount of 2.0 percent by mass. The mixture was pre-dispersed using a homogenizer for 5 minutes to prepare a slurry. The average particle diameter as used herein is a volume average particle diameter.

Next, a cotton nonwoven fabric of 80 g/m² was dipped in the prepared slurry. Any excess of the slurry was removed, and the nonwoven fabric was dried at 120° C. for 10 minutes to obtain a wiping sheet having a virus inactivating effect.

Example 9

100.0 g of a powder of copper(I) thiocyanate in Reference Example 25 that was used as fine particles having a virus inactivating ability was pre-dispersed in 900.0 g of ethanol, and the particles were pulverized and dispersed using a bead mill to obtain a slurry having an, average particle diameter of 104 nm.

Then methacryloxypropyltrimethoxy silane (KBM-503, product of Shin-Etsu Chemical Co., Ltd.), a silane monomer having an unsaturated bond, was subjected to dehydration-condensation by an ordinary method to covalently-bond the silane to the surfaces of zirconium oxide particles (PCS, product of Nippon Denko Co., Ltd.), and the resultant particles were used as the second inorganic fine particles. 100 g of the second inorganic fine particles were pre-dispersed in ethanol and were pulverized and dispersed using a bead mill to obtain a slurry having an average particle diameter of 20 nm. The average particle diameter as used herein is a volume average particle diameter.

The above two types of slurries were added in a mixing ratio of 40 percent by mass of the copper thiocyanate dispersion and 60 percent by mass of the zirconium oxide particle dispersion were mixed, and ethanol was added to the mixture such that the concentration of the solid was adjusted to 5 percent by mass.

Then the resultant slurry was applied to a rayon nonwoven fabric of 80 g/m² by spraying, and the nonwoven fabric was dried to obtain a wiping sheet having a virus inactivating effect.

Example 10

A powder of copper(I) chloride in Reference Example 22 was used as fine particles having a virus inactivating ability and was pulverized into an average particle diameter of 350 nm using a dry pulverizer, Nano Jetmizer (product of Aishin Nano Technologies CO., Ltd.). The average particle diameter as used herein is a volume average particle diameter. TL-0511, a product of SEKISUI FULLER, used as a reactive hot-melt adhesive was ejected in a filament form from an ALTA signature spray gun, manufactured by Nordson K.K., to produce a fiber structural body having adhesive properties. Then the pulverized copper(I) chloride fine particles were brought into contact with the fiber surfaces of the fiber structural body. The resultant fiber structural body was allowed to react in an environment of a humidity of 60% and 50° C. for 4 hours to cure the reactive hot melt, and a filter was thereby obtained.

Example 11

A powder of copper(I) chloride in Reference Example 22 was used as fine particles having a virus inactivating ability and was pulverized into an average particle diameter of 350 nm using a dry pulverizer, Nano Jetmizer (product of Aishin Nano Technologies CO., Ltd.). The pulverized copper(I) chloride was added to ethanol in an amount of 0.5 percent by mass, and tetramethoxy silane (KBM-04, product of Shin-Etsu Chemical Co., Ltd.) was further added in an amount of 0.4 percent by mass. The mixture was pre-dispersed using a homogenizer for 5 minutes to prepare a slurry. The average particle diameter as used herein is a volume average particle diameter.

Next, a polyester film (product of TORAY Industries, Inc.) having a thickness of 125 μm was hydrophilized by corona treatment and was coated with the coating solution prepared in Example 11 using a bar coater, and the resultant film was dried at 110° C. for one minute. Then the film was irradiated with an electron beam at an acceleration voltage of 200 kV and 50 kGy to obtain a virus inactivating film sheet having a virus inactivating effect.

Example 12

A powder of copper(I) oxide in Reference Example 27 was used as fine particles having a virus inactivating ability and was pulverized into an average particle diameter of 460 nm using a dry pulverizer, Nano Jetmizer (product of Aishin Nano Technologies CO., Ltd.). The pulverized copper(I) oxide fine particles were added to ethanol in an amount of 4.0 percent by mass, and tetramethoxy silane (KBM-04, product of Shin-Etsu Chemical Co., Ltd.) was further added in an amount of 0.4 percent by mass. The mixture was pre-dispersed using a homogenizer for 5 minutes to prepare a slurry. The average particle diameter as used herein is a volume average particle diameter.

Then the prepared slurry was applied to a rayon nonwoven fabric of 80 g/m$^2$ by spraying, and the nonwoven fabric was dried at 120° C. to obtain a virus inactivating nonwoven sheet having a virus inactivating effect.

Example 13

100.0 g of a powder of copper(I) oxide in Reference Example 27 that was used as fine particles having a virus inactivating ability was pre-dispersed in 900.0 g of ethanol, and the particles were pulverized and dispersed using a bead mill to obtain a slurry having an average particle diameter of 210 nm.

Then methacryloxypropyltrimethoxy silane (KBM-503, product of Shin-Etsu Chemical Co., Ltd.), a silane monomer having an unsaturated bond, was subjected to dehydration-condensation by an ordinary method to covalently-bond the silane to the surfaces of zirconium oxide particles (PCS, product of Nippon Denko Co., Ltd.), and the resultant particles were used as the second inorganic fine particles. 100 g of the second inorganic fine particles were pre-dispersed in ethanol and were pulverized and dispersed using a bead mill to obtain a slurry having an average particle diameter of 20 nm. The average particle diameter as used herein is a volume average particle diameter.

The above-prepared slurries were mixed in a mixing ratio of 40 percent by mass of the pulverized copper(I) oxide fine particles and 60 percent by mass of the zirconium oxide particles, and ethanol was added to the mixture such that the concentration of the solid was adjusted to 5 percent by mass.

Next, a vinyl chloride wallpaper sheet (dinoc (registered trademark), product of Sumitomo 3M Limited) having a thickness of 200 μm was hydrophilized by corona treatment and then coated with the coating solution prepared in Example 13 using a bar coater, and the resultant sheet was dried at room temperature to obtain a virus inactivating vinyl chloride sheet having a virus inactivating effect.

Comparative Example 1

A rayon nonwoven fabric of 18 g/m$^2$ (product of KURARAYKURAFLEX Co., Ltd.) was used as a nonwoven fabric in Comparative Example 1.

Comparative Example 2

A nonwoven fabric sheet of Comparative Example 2 was produced under the same conditions as in Example 1 except that the fine particles having a virus inactivating ability and used in Example 1 were not added.

Comparative Example 3

A polyester monofilament mesh of 305 mesh (product of NBC Meshtec Inc.) was used as a mesh sheet of Comparative Example 3.

Comparative Example 4

A mesh sheet of Comparative Example 4 was produced under the same conditions as in Example 2 except that the fine particles having a virus inactivating ability and used in Example 2 were not added.

Comparative Example 5

A nonwoven fabric sheet of Comparative Example 5 was produced under the same conditions as in Example 3 except that the fine particles having a virus inactivating ability and used in Example 3 were not added.

Comparative Example 6

A polyester film (product of TORAY Industries, Inc.) having a thickness of 125 μm was obtained as a film sheet of Comparative Example 6.

Comparative Example 7

A film sheet of Comparative Example 7 was produced under the same conditions as in Example 4 except that the fine particles having a virus inactivating ability and used in Example 4 were not added.

Comparative Example 8

A cotton nonwoven fabric sheet of Comparative Example 8 was produced under the same conditions as in Example 8 except that the fine particles having a virus inactivating ability and used in Example 8 were not added.

Comparative Example 9

A hot melt nonwoven fabric sheet of Comparative Example 9 was produced under the same conditions as in Example 10 except that the fine particles having a virus inactivating ability and used in Example 10 were not added.

Comparative Example 10

A vinyl chloride wallpaper sheet of Comparative Example 13 was produced under the same conditions as in Example 13 except that the fine particles having a virus inactivating ability and used in Example 13 were not added.

Method of Evaluating Antiviral Ability in the Present Invention

In the measurement of the virus inactivating ability of a virus inactivating sheet, an influenza virus (influenza A/Kitakyusyu/159/93(H3N2)) cultured in MDCK cells was used as a virus having an envelope, and a feline calicivirus generally used as an alternative to a norovirus was used as a virus having no envelope.

When a nonwoven fabric sheet or a mesh sheet was used as a virus inactivating sheet, a sample (2 cm×2 cm, a four-ply sheet) was placed in a sterilized vial. Then 0.1 mL of a virus solution was added dropwise thereto and allowed to react at room temperature for 60 minutes. After the reaction for 60 minutes, 1900 μL of a 20 mg/mL bouillon protein solution was added, and the virus was washed off by pipetting. Then the reaction sample was diluted with an MEM diluting solution until $10^{-2}$ to $10^{-5}$ (ten-fold serial dilution). 100 μL of the sample solutions were inoculated on MDCK cells cultured in petri dishes. After the resultant cells were allowed to stand for 90 minutes to adsorb the virus onto the cells, a 0.7% agar medium was placed thereon, and the virus was cultured at 34° C. in 5% of $CO_2$ for 48 hours in an incubator. After formalin-fixation and methylene blue staining were performed, the number of plaques formed was counted to compute the infectivity titer of the virus (PFU/0.1 mL, Log 10) (PFU: plaque-forming units).

When a film sheet was used, a sample (5 cm×5 cm) was placed in a plastic petri dish. Then 0.1 mL of a virus solution was added dropwise thereto and allowed to react at room temperature for 60 minutes. The upper surface of the test sample was covered with a PP film (4 cm×4 cm) to make the area of contact between the virus solution and the test sample uniform during the test. After the reaction for 60 minutes, 1900 μL of a 20 mg/mL bouillon protein solution was added, and the virus was washed off by pipetting. Then the infectivity titer (PFU/0.1 mL, Log 10) (PFU: plaque-forming units) was computed by the plaque method.

Evaluation of Antiviral Ability of the Present Invention

The antiviral ability was evaluated for each of Examples 1 to 13 and Comparative Examples 1 to 10. The evaluation results are shown in Tables 3 and 4. The values obtained when a virus solution was covered with a PP film without placing a sample were used as the values for the control.

TABLE 3

| | INFECTIVITY TITER (PFU/0.1 ml, Log10) | |
| --- | --- | --- |
| | INFLUENZA | FELINE CALICIVIRUS |
| EXAMPLE1 | <1 | <1 |
| EXAMPLE2 | <1 | <1 |
| EXAMPLE3 | <1 | <1 |
| EXAMPLE5 | <1 | <1 |
| EXAMPLE6 | <1 | <1 |
| EXAMPLE7 | <1 | <1 |
| EXAMPLE8 | <1 | <1 |
| EXAMPLE9 | <1 | <1 |
| EXAMPLE10 | <1 | <1 |
| EXAMPLE12 | <1 | <1 |
| COMPARATIVE EXAMPLE1 | 5.96 | 5.45 |
| COMPARATIVE EXAMPLE2 | 5.64 | 5.62 |
| COMPARATIVE EXAMPLE3 | 5.97 | 5.60 |
| COMPARATIVE EXAMPLE4 | 5.83 | 5.81 |
| COMPARATIVE EXAMPLE5 | 5.70 | 5.79 |
| COMPARATIVE EXAMPLE8 | 5.64 | 5.51 |
| COMPARATIVE EXAMPLE9 | 5.81 | 5.50 |
| CONTROL | 6.02 | 5.95 |

TABLE 4

| | INFECTIVITY TITER (PFU/0.1 ml, Log10) | |
| --- | --- | --- |
| | INFLUENZA | FELINE CALICIVIRUS |
| EXAMPLE4 | <1 | <1 |
| EXAMPLE11 | <1 | <1 |
| EXAMPLE13 | <1 | <1 |
| COMPARATIVE EXAMPLE6 | 6.01 | 5.40 |
| COMPARATIVE EXAMPLE7 | 5.84 | 5.90 |
| COMPARATIVE EXAMPLE10 | 5.70 | 5.76 |
| CONTROL | 6.02 | 5.95 |

As can be seen from the above results, the virus inactivating effect on the two viruses was higher in all the Examples than in the Comparative Examples. The effect observed was very high, i.e., the inactivation ratio after 60 minutes was 99.9999% or higher. Therefore, with these sheets, an environment with a reduced risk of virus infection can be provided.

REFERENCE SIGNS LIST 1 sheet body
2 virus inactivating fine particle
3 silane monomer or oligomer
4 binder (reinforcing agent)
5 chemical bond
6 second inorganic fine particle
7 adhesive
100 virus inactivating sheet

The invention claimed is:

1. A virus inactivating sheet capable of inactivating a virus adhering thereto, comprising
a sheet body; and
monovalent copper compound fine particles and/or iodide fine particles, the monovalent copper compound fine particles and/or the iodide fine particles being held by the sheet body,
wherein the monovalent copper compound fine particles and/or the iodide fine particles are held on the virus inactivating sheet as three-dimensional aggregates forming fine irregularities on a surface of the virus inactivating sheet,
the monovalent copper compound fine particles are particles of at least one selected from the group consisting of CuCl, $CuOOCCH_3$, CuI, CuBr, $Cu_2S$, and CuSCN,
wherein the virus inactivating sheet further comprises a group of other inorganic fine particles formed by binding the other inorganic fine particles to each other through chemical bonds with a silane monomer and/or an oligomer thereof in the three-dimensional aggregates, and
wherein the group of the other inorganic fine particles is fixed to the sheet body through chemical bonds with a silane monomer and/or an oligomer thereof, and the monovalent copper compound fine particles and/or the iodide fine particles are held on the sheet body so as to be entangled with the group of other inorganic fine particles.

2. The virus inactivating sheet according to claim 1, characterized in that the iodide fine particles are particles of at least one selected from the group consisting of CuI, AgI, $SbI_3$, $IrI_4$, $GeI_2$, $GeI_4$, $SnI_2$, $SnI_4$, TlI, $PtI_2$, $PtI_4$, $PdI_2$, $BiI_3$, AuI, $AuI_3$, $FeI_2$, $CoI_2$, $NiI_2$, $ZnI_2$, HgI, and $InI_3$.

3. A bed sheet using the virus inactivating sheet according to claim 1.

4. A protective suit using the virus inactivating sheet according to claim 1.

5. A glove using the virus inactivating sheet according to claim 1.

6. A medical drape using the virus inactivating sheet according to claim 1.

7. A cap using the virus inactivating sheet according to claim 1.

8. A shoe cover using the virus inactivating sheet according to claim 1.

9. A filter using the virus inactivating sheet according to claim 1.

10. A surgical tape using the virus inactivating sheet according to claim 1.

11. Gauze using the virus inactivating sheet according to claim 1.

12. Wallpaper using the virus inactivating sheet according to claim 1.

* * * * *